(12) United States Patent
Sengupta et al.

(10) Patent No.: US 8,158,806 B2
(45) Date of Patent: Apr. 17, 2012

(54) DAT1

(75) Inventors: Suparna Sengupta, Trivandrum (IN); Kallikat Narayanan Rajasekharan, Trivandrum (IN)

(73) Assignees: Department of Biotechnology, New Delhi (IN); Rajiv Gandhi Centre for Biotechnology; University of Kerala

( * ) Notice: Subject to any disclaimer, the term of this patent is extended or adjusted under 35 U.S.C. 154(b) by 701 days.

(21) Appl. No.: 12/209,646

(22) Filed: Sep. 12, 2008

(65) Prior Publication Data

US 2009/0018341 A1  Jan. 15, 2009

Related U.S. Application Data

(62) Division of application No. 11/578,566, filed as application No. PCT/IN2004/000108 on Apr. 16, 2004, now abandoned.

(51) Int. Cl.
*C07D 277/42* (2006.01)
(52) U.S. Cl. ...................................................... 548/191
(58) Field of Classification Search .................... 548/191
See application file for complete search history.

(56) References Cited

OTHER PUBLICATIONS

K. N. Rajasekharan et al., "Studies on the Synthesis of 5-Acyl-2,4-diaminothiazoles from Amidinothioureas," May 1986, Synthesis, No. 5, pp. 353-355.
R. Binu et al., "Synthesis and cyclization of 1-(N-nitroamidion)thioureas to 2,4-diaminothiazoles," 1998, Organic Preparations and Procedures International, vol. 30, No. 1 pp. 93.

*Primary Examiner* — Laura L. Stockton
(74) *Attorney, Agent, or Firm* — The Webb Law Firm

(57) ABSTRACT

A synthetic diaminoketothiazole, its process of preparation and its use as a microtubule inhibitor, a probe for tubulin-microtubule system and a cytotoxic agent. Diaminoketothiazole of the formula (I) wherein Ar is 4-OMe-$C_6H_5$, Ar' is $C_6H_5$.

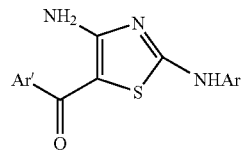

3 Claims, 2 Drawing Sheets

DAT1

CROSS REFERENCE TO RELATED APPLICATIONS

Figure 1:
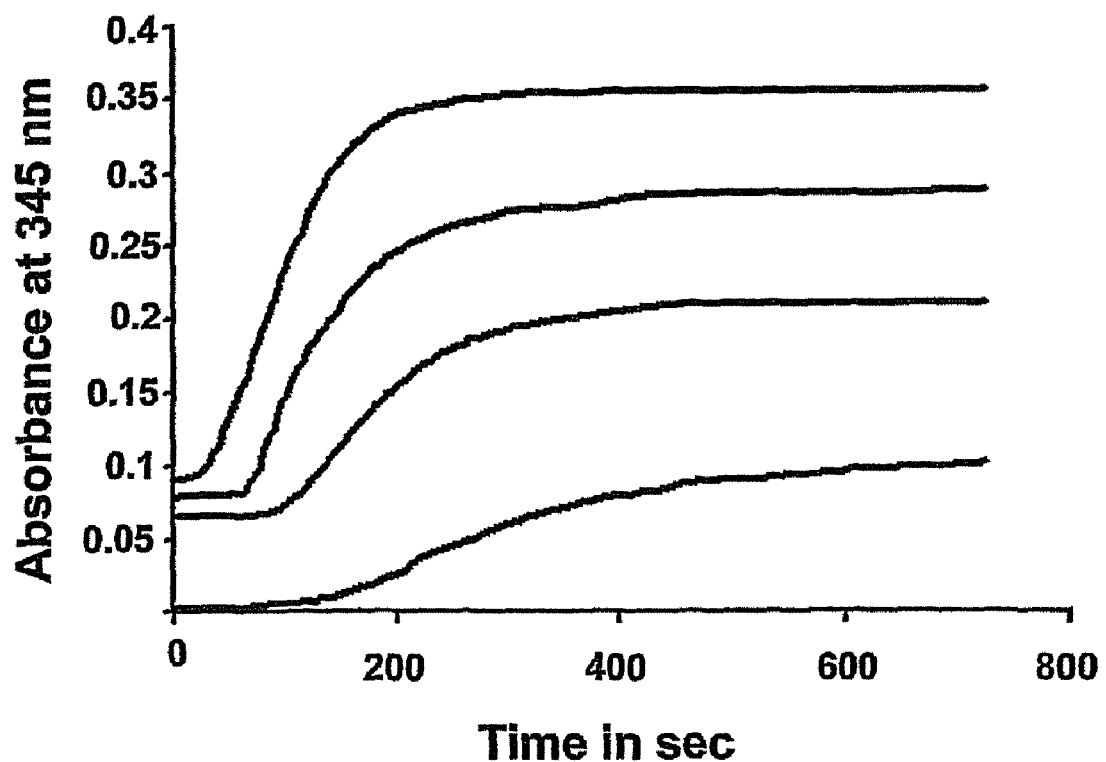

This application is a divisional of U.S. patent application Ser. No. 11/578,566 filed Jan. 8, 2008 and entitled "DAT1", now abandoned, which was the United States national phase application of PCT/IN2004/000108 filed Apr. 16, 2004, all of which are incorporated herein by reference in their entirety.

FIELD OF THE INVENTION

This invention relates to Diaminoketothiazole (DAT1) and to the process of preparation thereof.

Further this invention also relates to the use of Diaminoketothiazole (DAT1) as a microtubule inhibitor, a probe for tubulin-microtubule system and a cytotoxic agent.

BACKGROUND OF THE INVENTION

Microtubules are a topic of intense research because of their important and multiple functions in the cell. Many of the potential anticancer agents act on microtubules and arrest mitosis as during mitotic cell division, microtubules play a crucial role by maintaining proper spindle function. Microtubule effectors work in two ways, they can interfere with microtubule dynamics and they can shift the tubulin-microtubule equilibrium in the cell by either inducing or inhibiting microtubule polymerization. There are three major classes of microtubule effectors. Taxanes stabilize microtubules by blocking disassembly. Vinca alkaloids and colchicine site binders destabilize microtubules by the inhibition of assembly of tubulin molecules, the major component of microtubules. Taxanes like Paclitaxel, docetaxel and vinca alkaloids like vincristine and vinblastine are well characterized and widely used clinically in different types of malignancies.

The main drawback of Taxanes and vinca alkaloids is that their use is limited by the development of drug resistance, neurotoxicity and limited availability leading to very high expenses involved.

The derivatives of diaminoketothiazoles have received much attention lately as inhibitors of cyclin-dependent kinases and glycogen synthase kinase-3. These are thus claimed to be useful Sir fee treatment of malignancies and Alzhemer's disease, impaired glucose tolerance, Type 1 and 2 diabetes.

For the synthesis of diaminoketothiazole, there exists only few methods. The first method makes use of a cyanothiourea derivative to provide the (C-N-C-S) atoms required for the thiazole construction and the remaining C atom is sourced from an alpha-haloketone. The second method utilizes thiocarbamoylamidine derivatives as fee source of the (C-N-C-S) four-atom complement In the third approach, an S-alkyldithiobiuret serves as synthon for providing the (C-N-C-S) four-atom complement. These methods are usually suited for the solution phase synthesis of the title compounds. However, in the light of combinatorial library synthesis, solid phase methods are much more desirable. Such approaches allow rapid synthesis of a large number of analogue molecules that can be later subjected to bioactivity screening.

SUMMARY OF THE INVENTION

An object of this invention is to propose a Diaminoketothiazole (DAT1) and a novel process for the preparation thereof.

Another object of this invention is to propose a new solid phase synthesis of diaminoketothiazole.

Further object of this invention is to propose a useful method for the synthesis of diaminoketothiazoles on a solid support.

Still further object of this invention is to propose a process of synthesis of diaminoketothiazoles (DAT1) which is cheap and cost effective.

Another object of this invention is to propose DAT1 as a microtubule inhibitor and cytotoxic agent.

Still another object of this invention is to propose diaminoketothiazoles for the treatment of cancer and other disease using its microtubule inhibition activity. Yet another object of this invention is to propose diaminoketothiazoles as a probe for structure-function studies of tubulin-microtubule system.

DETAILED DESCRIPTION OF THE INVENTION

According to this invention mere is provided a Diaminoketothiazole (DAT1). Further, according to this invention there is also provided a process for the solid phase synthesis of diaminoketothiazoles comprising, reacting aminomethylpolystyrene beads with 1-[N-(arylthiocarbamoyl) amidino]-3,5-dimethylpyrazole to produce N-(N-arylthiocarbamoyl)-N-guanidinomethyl polystyrene (2);

reacting said N-(N-arylthiocarbamoyl)-N-guanidinomethyl polystyrene with alpha haloketones in the presence of a base which produces the acyclic S-alkyl intermediate derivative (3);

subjecting the said intermediate thus formed directly, without isolation, to the step of cyclisation to obtain the intermediate cyclic thiazoline (4);

subjecting the intermediate thus formed to a step of eliminative aromatization again directly, without isolation, to produce diaminoketothiazole in the solution; filtering the said solution to remove the polymer beads, if any, and impurities and subsequently isolating 5-aroyl-4-amino-2-arylaminothiazoles from the solution by precipitation.

According to another embodiment of this invention, there is provided the use of diaminoketothiazole as a microtubule inhibitor, a tubulin binding agent and a cytotoxic agent.

DESCRIPTION OF THE ACCOMPANYING FIGURES:

FIG. 1. Time-course of inhibition of in vitro microtubule assembly by DAT1. 1.2 mg/ml of 3X MTP was incubated wife different concentrations of DAT1 for 2 min at 24° C. in PEM buffer. Subsequently 1 mM GTP was added and polymerization was followed by the turbidity at 345 nm for 20 min at 37° C. Control MTP (1), MTP with 10 µM DAT1 (2), 20 µM DAT1 (3) and 40 µM DAT1 (4).

Figure 2:
Figure 2:
Figure 2:
Figure 2:
Figure 2:
Figure 2:

FIG. 2: Effect of DAT1 on the microtubule network HeLa cells were exposed to DMSO (A & B), 1 µM (C) or 0.2 µM (D) DAT1 and 0.1 µM (E) or 0.02 µM (F) vinblastine. After 24 h, microtubules were visualized by indirect immunofluorescence microscopy using an antibody against β-tubulin.

DETAILED DESCRIPTION OF THE INVENTION

The present invention relates to the solid phase synthesis of diaminoketothiazole on polymer beads. The details of the new invention is described below.

Polymer beads comprising DVB-cross linked chloromethylpolystyrene such as 2% by wt, was converted to aminomethylpolystyrene (AMPS) by a reported method. The aminomethylpolystyrene beads so obtained were then reacted by a new method with 1-[(N-arylthiocarbamoyl)amidino]-3,5-dimethylpyrazole 1which acts as a thiocarbamoyl group transfer agent. This converts fee amino group on fee polymer bead into a N-(N-arylthiocarbamoyl)guanidine group giving novel N-(N-arylthiocarbamoyl)-N'-guanidinomethyl polystyrene 2 (AGMPS). his on reaction wife alpha haloketones in fee presence of abase gives the acyclic S-alkyl intermediate derivative 3, which then directly and in citu undergoes a cyclisation to fee next intermediate cyclic thiazoline 4, followed by an eliminative aromatization step in which the aminomethyl polystyrene acts as a leaving group, thus leading to fee release of diaminoketothiazole 5 in solution. A filtration removes the polymer, dilution of fee solvent wife water cleanly precipitates the product 5-aroyl-4-amino-2-arylaminothiazoles 5.

Reaction Scheme

DAT1 distorts microtubules in HeLa cells as well as inhibits the in vitro assembly of microtubular proteins. It exhibits cytotoxicity in different types of cancer cell lines and is much more active than paclitaxel and somewhat more active than vinblastine is drug resistant cancer cells. It is much less toxic to normal cells than cancer cells. Moreover, its synthesis is quite cheap compared to the cost involved in the synthesis of taxanes and vinca alkaloids.

The compound DAT1 was tested for its cytotoxicity on human cervical, uterus and colon cancer cell lines and mouse fibrocercoma cells. Cell lines were obtained from ATCC, USA and NCCS, Pune, India. MTT assay, which correlates a fomazan dye formation wife the number of viable cells, was used for this purpose. The widely used anticancer drugs paclitaxel, vinblastine or the antimitotic drug colchicine were used for comparison. In 5 out of the 9 cell lines tested, DAT1 showed activity wife $IC_{50}$ values in a range of 0.05-0.3 µM, and in 2 cell lines, the values were in the range of 1-5 µM (Table 1). These values were either comparable or 5-20 times lower than paclitaxel and vinblastine. Subsequently, DAT1 was tested on fee multidrug resistant cell line MES-SA/DX5, which is resistant to a number of important antimitotic and anticancer agents, viz, colchicine, paclitaxel, vinca alkaloids, doxorubicin etc. It was found to be 15 and 2 times more active than paclitaxel and vinblastine respectively.

The cell survival in fee normal immortalized cell line IMR 90 (lung epithelial) was good after fee treatment of DAT1 in a concentration which was much more than the $IC_{50}$ values in all fee cancer cell lines tested. In comparison, fee cell survival was less upon vinblastine treatment and similar upon paclitaxel treatment in similar concentrations (data not shown).

As many of the potential anticancer drugs are antimitotic and microtubule effectors, DAT1 was tested for its effect on microtubule assembly. A spectrophotometric assay was used for this purpose where turbidity at 350 nm was used to quantitate the amount of microtubule polymers formed from microtubular proteins. FIG. 1 shows mat it inhibited microtubule formation in a concentration dependent manner.

The in vivo effect of DAT1 on microtubules was tested on HeLa (cervical cancer cell line) cells after an incubation of 48 hours and staining the microtubule network by an antitubulin antibody followed by a Rhodamine labeled secondary antibody. FIG. 2 shows that microtubule network was destroyed by DAT1 in a similar manner to the anticancer drug, vinblastine.

As tubulin is the major component of microtubules, the effect of DAT1 on purified tubulin was checked. DAT1 absorbs light with absorption maxima at 212 nm, 283 nm and 374 nm in methanol. Although DAT1 doesn't exhibit any fluorescence by itself in aqueous solution, when incubated with tubulin, it showed fluorescence with an emission maximum of 457 nm upon excitation at 374 nm. The fluorescence intensity increased with the increase in concentration of tubulin showing mat it bound to tubulin.

To measure the binding affinity and stoichiometry of DAT1 binding to tubulin, a titration of tubulin wife DAT1 at 24° C. was performed and me fluorescence values at 450 nm were noted upon excitation at 374 nm. A $K_d$ (Dissociation constant) value of 2.9±1 µM and a stoichiometry of 1 were calculated (mean of three experiments) from a scatchard plot.

All these observations place DAT1 in a suitable position for consideration as a good microtubule inhibitor, a suitable probe for the structure-function studies of tubulin-microtubule system and a potential anticancer agent. The physical (IR spectral, NMR and MS spectral) date, are shown in Table 2.

EXAMPLES

1. Conversion of aminomethylpolystyrene (AMPS) to N-(N-arylthiocarbamoyl)-N-guanidinomethyl polystyrene 2 (AGMPS)-General Procedure Aminomethylpolystyrene resin beads (2 g, 2.13 meq. $NH_2$/g resin) was swelled in acetonitrile (5 ml). To the swelled resin, a solution of 1-[(N-arylthiocarbamoyl)amidno]-3,5-dimethylpyrazole 1 (2 molar equivalents) in acetonitrile (10 mL) was added. The mixture was then refluxed for 12-15 h. The resin beads were men removed by filtration, washed repeatedly with warm and men cold acetonitrile (3×10 ml), men wife petroleum ether (60-80° b.p) (2×10 ml) and then dried in vacuum. The S capacity of the resin was men estimated by digestion and gravimetry by standard procedures. This was found to be in the range 0.98-1.32 meg/g resin.

2. Synthesis of 5-acyl-4-amino-2 arylaminothiazoles 5:
General Procedure:

The above arylthiocarbamoyl resin (AGMPS) was swelled in N,N-dimethyl formanide (DMF) (5 ml). To this, the respective α-bromoketone (molar equivalent as per S-capacity) in DMF (2 ml) was added followed by two molar equivalents of triethylamine.

The mixture was warmed to 50-60° C. for 2-5 b. The resin beads were removed by filtration, washed with DMF and the pooled filtrate and washings were carefully diluted by ice-cold water (100 ml). The precipitated 5-aroyl-4-amino-2-arylaminothiazoles 5 were collected by filtration and purified by crystallization or column chromatography on silica gel. A few typical results in the preparation of thiazole 5 is given below.

| No | Ar | Ar' | Yield % |
|---|---|---|---|
| 5a | $C_6H_5$ | $C_6H_5$ | 65-68 |
| 5b | 4-Cl—$C_6H_4$ | $C_6H_5$ | 73-78 |
| 5c | 4-Me—$C_6H_5$ | $C_6H_5$ | 68-72 |
| 5d | 4-OMe $C_6H_5$ | $C_6H_5$ | 67-71 |

3. Cell Viability Assay: MTT assay was used to determine fee number of viable cells upon drug addition. Cells were seeded in microtitre plates (generally 5×10³ cells per well) and were incubated with different concentrations of the cytotoxic agents for 48 h. Subsequently, 100 µl of MTT solution (0.6 mg/ml) was added per well and incubated at 37° C. for additional 2 h. The amount of formazan salt was quantified in quadruplicates by recording fee absorbance at 570 ran using a Biorad Plate reader. The growth inhibition constants ($IC_{50}$) were calculated from the semi logarithmic dose response plots using fee nonlinear regression program Origin. All the experiments were done for at least three times.

4. Microtubule and Tubulin Preparation: Microtubular protein was prepared from goat brains by two cycles of temperature dependent assembly-disassembly process in PEM buffer (100 mM PIPES, pH 6.9, 1 mM $MgCl_2$ & 1 mM EGTA ) with 1 mM GTP at 37° C. For fee polymerization experiments, it was followed by one more cycle in PEM. Tubulin was purified from 2X MTP using glutamate buffer for assembly.

5. Polymerization assay: MTP polymerization, in fee presence or absence of DAT1, was measured by the time course of fee turbidity at 37° at 345 nm. A Shimadzu UV-1601 double beam spectrophotometer fitted with a temperature-controlled circulating water bath was used for this purpose.

6. Immunofluorescence assay: HeLa cells were incubated with the drug for 24 h at 37° C., washed with PBS and fixed with 4% paraformaldehyde at 4° C. Subsequently, they were washed and permeabilized with 0.2% Triton X-100 in PBS for 20 min at 37° C. Microtubules were stained by a mouse monoclonal antibody against β-tubulin in 1:100 dilution followed by a Rhodamine conjugated goat anti-mouse antibody in 1:50 dilution and were observed by a Nikon Eclipse TE300 microscope.

7. Tubulin binding: Emission spectra of DAT1 in presence of tubulin were recorded from 400 nm to 600 nm using an excitation wavelength of 374 nm. Excitation and emission bandpasses are 2.5 nm each and the fluorescence values recorded are uncorrected. All fluorescence measurements were performed in a Perkin-Elmer model LS50B Luminescence spectrometer.

The binding parameters of DAT1 binding to tubulin were measured from fluorescence data by the standard Scatchard analysis. The binding constants and stoichiometries were determined from Scatchard plot using 2 μM tubulin and varying DAT1 over 0.2-20 μM. Fluorescence values were recorded at 450 nm using an excitation wavelenglh of 350 nm to reduce the absorbance of DAT1. Inner filter effect correction were performed to minimize the effect of high absorbance of the fluorophore.

TABLE 1

Cytotoxic activity of DAT1 against different tumour cell lines

| Cell Lines | $IC_{50}$ values | | | |
|---|---|---|---|---|
| (Source) | DAT1 | Paclitaxel | Vinblastine | Colchicine |
| HCT 116 (Human colon) | 0.3 μM | 0.012 μM | 0.005 μM | |
| HeLa (Human cervix) | 0.054 μM | 0.034 μM | 0.001 μM | |
| L-929 (Mouse connective tissue) | 1 μM | 0.3 μM | | |
| CaSki (Human cervix) | 0.2 μM | 0.02 μM | | 0.25 μM |
| SW 620 (Human colon) | 0.2 μM | 0.007 μM | 0.2 μM | |
| SiHa (Human cervix) | 5 μM | 1.1 μM | | 2.5 μM |
| MES-SA/Dx5 (Human uterus) | 0.35 μM | 8.6 μM | 0.73 μM | |

Different concentrations of DAT1, paclitaxel and vinblastine or colchicine were incubated at 37° C. with the different cell lines. After 48 hours, drug containing media were removed and MTT assay were done as described in the examples. $IC_{50}$ values (growth inhibition constants) were calculated using the nonlinear regression program Origin. The average of three experiments is shown.

TABLE 2

Physical data of DAT1

| | |
|---|---|
| Ar' | $C_6H_5$— |
| Ar | 4-$CH_3O$—$C_6H_4$- |
| m.p° C. | 205-6 |
| Yield % | 67-71% |
| IR (KBr) $cm^{-1}$ | 3344, 3179, 1600, 1557, 1513, 1459, 1366, 1251, 1169, 1108, 1058, 1025, 912, 743, 705. |
| $^1$H NMR δ | 3.82(s, 3H), 6.9-7.72(m, 9H), 8.15 (br, 2H). |
| MS m/z (%) | EIMS: 325 (24, M$^+$), 323 (11), 248 (3), 220 (5), 165 (7), 149 (15), 148(8), 134(11), 133(16), 122(16), 105(58), 78(26), 77(100) |

We claim:

1. A process for preparing diaminoketothiazole (DAT1), of the following formula, wherein Ar represents 4-OMe-$C_6H_4$ and Ar' represents $C_6H_5$

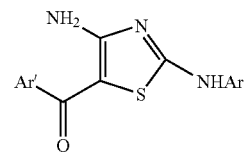

comprising:
reacting aminomethylpolystyrene beads and 1-[N-(arylthiocarbamoyl) amidino]-3,5-dimethylpyrazole to produce N-(N-arylthiocarbamoyl)-N-guanidinomethyl polystyrene;
reacting said N-(N-arylthiocarbamoyl)-N-guanidinomethyl polystyrene with an α-haloketone in the presence of a base which produces an acyclic S-alkyl intermediate derivative;
subjecting the acyclic S-alkyl intermediate derivative to the step of cyclisation to obtain an intermediate cyclic thiazoline;
subjecting the cyclic thiazoline intermediate to the step of eliminative aromatization to produce diaminoketothiazole in a solution;
filtering said solution to remove impurities; and
then isolating 5-aroyl-4-amino-2-arylaminothiazoles from the solution by precipitation.

2. The process as claimed in claim 1, wherein said α-haloketone is α-bromoketone.

3. The process as claimed in claim 1, wherein said step of precipitation is done by using ice-cold water.

* * * * *

UNITED STATES PATENT AND TRADEMARK OFFICE
CERTIFICATE OF CORRECTION

| | | |
|---|---|---|
| PATENT NO. | : 8,158,806 B2 | Page 1 of 1 |
| APPLICATION NO. | : 12/209646 | |
| DATED | : April 17, 2012 | |
| INVENTOR(S) | : Suparna Sengupta et al. | |

It is certified that error appears in the above-identified patent and that said Letters Patent is hereby corrected as shown below:

Face of the Patent, Column 2, Item (56) References Cited, OTHER PUBLICATIONS, Line 5, delete "nitroamidion)" and insert -- nitroamidino) --

Signed and Sealed this
Twenty-eighth Day of August, 2012

David J. Kappos
*Director of the United States Patent and Trademark Office*